(12) United States Patent
Banfi et al.

(10) Patent No.: US 7,285,659 B2
(45) Date of Patent: Oct. 23, 2007

(54) PROCESS FOR THE PREPARATION OF D-RIBAVIRIN

(75) Inventors: Aldo Banfi, Milan (IT); Bruno Dall'Oro, Pedrengo (IT); Marco Frigerio, Milan (IT); Alfredo Mancini, Spinadesco (IT)

(73) Assignee: Archimica S.r.l., Milan (IT)

( * ) Notice: Subject to any disclaimer, the term of this patent is extended or adjusted under 35 U.S.C. 154(b) by 0 days.

(21) Appl. No.: 10/485,335

(22) PCT Filed: Jul. 29, 2002

(86) PCT No.: PCT/IB02/02950

§ 371 (c)(1),
(2), (4) Date: Jan. 30, 2004

(87) PCT Pub. No.: WO03/011884

PCT Pub. Date: Feb. 13, 2003

(65) Prior Publication Data

US 2004/0192904 A1    Sep. 30, 2004

(30) Foreign Application Priority Data

Jul. 30, 2001 (EP) .................................. 01830510

(51) Int. Cl.
  C07H 19/56  (2006.01)
  C07H 5/04  (2006.01)
(52) U.S. Cl. ................... 536/28.7; 536/55.3; 536/124
(58) Field of Classification Search ............. 536/28.7, 536/55.3, 124
  See application file for complete search history.

(56) References Cited

U.S. PATENT DOCUMENTS 3,798,209 A * 3/1974 Witkowski et al. ........ 536/26.9
6,130,326 A * 10/2000 Ramasamy et al. ........ 536/28.7

FOREIGN PATENT DOCUMENTS

JP    55 160793     12/1980
JP    55160793   * 12/1980

OTHER PUBLICATIONS

Revue Roumaine de Chimie, 1987, 32, 329-333.*
J.T. Witkowski, "Design, Synthesis, and Broad Spectrum Antiviral Activity of 1-β-D-Ribofuranosyl-1,2,4-triazole-3-carboximide and Related Nucleosides", J. Med. Chem. (1972), 15, pp. 1150-1154.
B. Shimizu and A. Saito, "The Synthesis of Ara-C Via β-D-Xylofuranosyl-cytosine Derivatives and of 'Virazole' by the Trimethylsilyl Ether 'Solution' Method", Nucl. Acid. Chem. (1978), 1, pp. 255-260.
H. Vorbrüggen, et al., "Nucleoside Synthesis with Trimethylsilyl Triflate and Perchlorate as Catalysts", Chemische Berichte, Verlag Chemie GmbH, vol. 114, pp. 1234-1255, (1981).
H. Vorbrüggen, et al., "On the Mechanism of Nucleoside Sytnhesis", Chem. Ber. (1981), 114, pp. 1256-1268.
C. Cristescu and C. Supuran, "as-Triazine Derivatives with Potential Therapeutic Actions. XXII. A Simplified Method for the Synthesis of 1,2,4-Triazole Nucleosides and 1,2,4-Triazine Nucleosides", Revue Roumaine de Chimie, vol. 32, pp. 329-333, (1987).
J. A. Marins, et al., "synthesis of Nucleosides Using Trimethylsilyl Perfluoroethoxyethanesulphonate as Catalyst", Nucleosides Nucleotides (1991), 10, pp. 619-620.
T. Green and P. Wuts in "Protecting Groups in Organic Synthesis, Third Edition", Chapter 2, p. 17-245, (1999).
K.S. Ramasamy, et al., "Monocyclic L-Nucleosides with Type 1 Cytokine-Inducing Activity", J. Med. Chem., (2000), 43, pp. 1019-1028.

* cited by examiner

Primary Examiner—Shaojia Anna Jiang
Assistant Examiner—Ganapathy Krishnan
(74) Attorney, Agent, or Firm—ProPat, L.L.C.

(57) ABSTRACT

A process for the preparation of ribavirin on an industrial scale is described which comprises the reaction of glycosylation of 3-substituted triazoles in the presence of a Lewis acid. Said process comprises:
 a) the reaction of a triazole of the formula

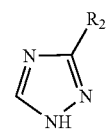

(I)

with a protected ribofuranose of the formula

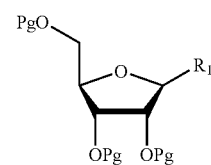

(II)

b) the removal of the Pg groups and, optionally, the conversion into a carboxyamide group of the $R_2$ group of the compound obtained of the formula

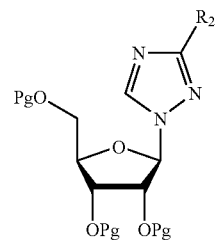

(III)

DD/mac—01.07.02.

17 Claims, No Drawings

PROCESS FOR THE PREPARATION OF D-RIBAVIRIN

Ribavirin, or 1-β-D-ribofuranosyl-1H-1,2,4-triazole-3-carboxyamide, is a known antiviral agent which is normally administered in association with alpha-2b interferon for treating patients affected by chronic hepatitis C.

TECHNICAL FIELD OF THE INVENTION

Ribavirin, (Merck Index 11th edition), the structure formula of which is given below,

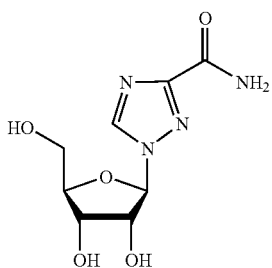

is generally prepared synthetically or fermentatively.

Particularly important among the processes for the synthetic preparation of ribavirin are the reactions of coupling of the preformed triazole nucleus with protected derivatives of sugar.

Such processes customarily provide for the activation of the preselected triazole nucleus with silylating agents and the subsequent reaction of the intermediate silyltriazole with the appropriate protected ribofuranose, according to the following general scheme:

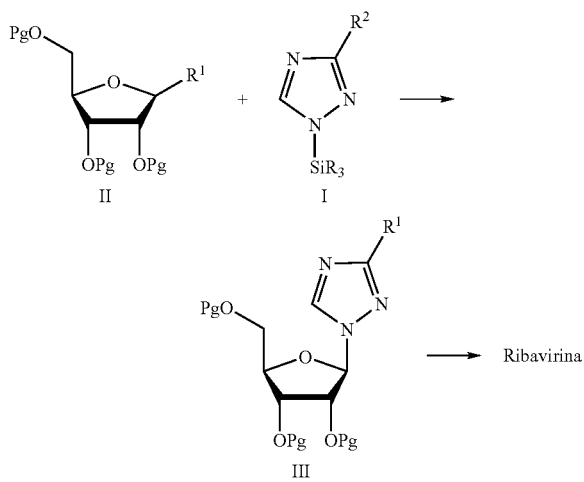

wherein $R^1$ usually represents an O-acetyl group or a halogen, Pg is a group protecting the hydroxyl function, such as for example acetyl or benzoyl, $R^2$ is preferably a carbomethoxy group and R represents alkyl, preferably methyl.

Ribavirin is then customarily obtained from the intermediate product III by de-protection of the sugar and conversion of the ester group into amide.

The sequence given above is described, for example, in *J. Med. Chem.* (1972), 15, 1150-1154.

However, the process has some drawbacks which make it of little applicative interest. In fact, in the glycosylation reaction in question there is obtained a raw product consisting of a 1:1 mixture of the desired product III, glycosylate on the triazole nitrogen in position 1, and of the glycosylate regioisomer on the nitrogen in position 2.

Consequently, not only is the final reaction yield significantly less than theory but, above all, the presence of large amounts of by-product necessitates the purification of the intermediate product IV by chromatography, with all the problems that said technique involves, especially in the case of industrial application.

Subsequently, the method of synthesis of ribavirin described above was the subject of numerous studies, from which different variants resulted, consisting essentially in the preparation in situ of the silylating agent [*Rev. Roum. Chim.* (1987), 32, 329-333], or in the use of a suitable acid catalyst. The latter reaction of silylation-glycosylation in the presence of acid catalysts, in particular Friedel-Crafts catalysts or Lewis acids, represents a standard methodology for preparing nucleosides [*Chem. Ber.* (1981), 114, 1256-1268] and, in various cases, this was applied specifically to the preparation of ribavirin.

To this end. Vorbrüggen et al., in *Chem. Ber.* (1981), 114, 1234-1255, studied the catalytic effect of silyltriflates with respect to the more conventional Lewis acids, such as, for example, $SnCl_4$ in the condensation of trimethylsilyltriazoles to give ribavirin precursors.

Another example of specific application of said synthetic procedure, catalysed by $HgBr_2$, is reported in *Nucl. Acid. Chem.* (1978), 1, 255-260.

Subsequently, an analogous synthesis of ribavirin, conducted in the presence of particular acid catalysts $(CF_3CF_2OCF_2CF_2SO_3SiMe_3)$, was presented at a symposium [*Nucleosides Nucleotides* (1991), 10, 619-20].

From a general evaluation of the literature pertaining to the above-mentioned synthesis of ribavirin, starting from the first work in 1972 up to the more recent work of 1991, the teaching clearly emerges that, in order to prepare ribavirin through glycosylation of the triazole, it is necessary to carry out preliminary activation thereof by silylation.

In fact, the publications mentioned above are characterised by the constant use of the silyltriazole for the specific reaction of glycosylation in question while experimental activity was directed to evaluating the influence of the acid catalysis on the reaction yield and on the composition of the final raw product. Apart from the reaction of silylation-glycosylation discussed hitherto, the synthesis of ribavirin may be conducted according to an alternative, rather drastic, fusion procedure. For example, the same article cited previously [*J. Med. Chem.* (1972), 15, 1150-1154] describes the preparation of ribavirin by fusion at 160-165° C. of a 1:1 mixture of 3-carbomethoxytriazole and tetra-acetylribose, in the presence of bis(p-nitrophenyl)phosphate. This process, however, the condensation yield of which is remarkably around 78% after crystallisation, is difficultly usable on an industrial level because of the rather critical conditions, such as the absence of solvent and the high temperature.

A new process has now been found for the preparation of ribavirin on an industrial scale, under particularly simple conditions and with high yields.

With respect to the procedures described in the prior art, the present invention makes it possible to prepare the intermediate product of the formula IV advantageously without the preliminary silylation of the triazole system and with a purity such as to permit the direct use of the raw reaction product in the subsequent stages, thus avoiding tedious purification processes.

Moreover, the rather mild reaction conditions make the present process particularly suitable for industrial application.

DESCRIPTION OF THE INVENTION

The subject of the present invention is therefore a process for the preparation of ribavirin which comprises:
a) the reaction of a triazole of the formula

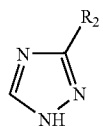

(I)

wherein $R_2$ represents a $C_1$-$C_4$ alkoxycarbonyl, arylalkoxycarbonyl, carboxyl, cyano, carboxyamide group with a protected ribofuranose of the formula

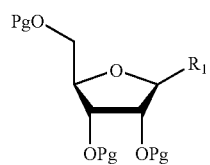

(II)

wherein Pg represents a group protecting the hydroxyl function and $R_1$ represents a leaving group selected from among $C_1$-$C_4$ acyloxy, aryloxy and halogen;
in the presence of a Lewis acid (IV); and
b) the removal of the Pg groups and, optionally, the conversion into a carboxyamide group of the $R_2$ group of the compound obtained of the formula

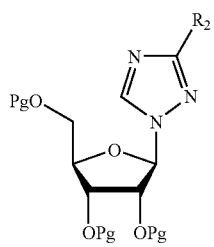

(III)

wherein Pg and $R_2$ have the meanings given above, to give ribavirin

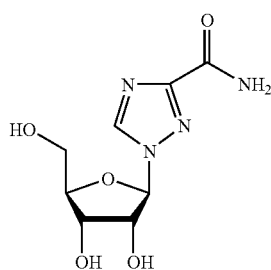

The starting triazole of the formula I can generally be prepared according to known procedures, for example as described in U.S. Pat. No. 3,798,209. Preferred compounds of the formula I are those in which $R_2$ represents a $C_1$-$C_4$ alkoxycarbonyl group, particularly those in which $R_2$ represents a carbomethoxy group.

The protected ribofuranose of the formula II can be prepared from ribose according to conventional techniques for protection of sugars or is commercially available.

According to the present invention, Pg represents a group protecting the hydroxyl function. Suitable protecting groups are generally ethers, esters, ketals and all the groups commonly used in the field of carbohydrate chemistry. See for example the groups described by T. Green and P. Wuts in "Protecting Groups in Organic Synthesis", chapter 2, page 17, 3rd Ed. (1999). Preferred protecting groups are acetyl, benzoyl and benzyl groups. In this context, the acetyl group is particularly preferred The $R_1$ group of the compound of the formula II represents a leaving group selected from among $C1_1$-$C_4$ acyloxy, aryloxy and halogen, preferably chlorine, bromine and $C_1$-$C_4$ acyloxy, and even more preferably acetoxy.

The present coupling reaction is conducted in the presence of a Lewis acid IV. For a definition of the term "Lewis acid" see, for example, J. March in "Advanced Organic Chemistry", page 227, 3rd Ed. (1985). According to the present invention, preferred Lewis acids are $AlCl_3$, $SbCl_5$, $BF_3$, $SnCl_4$ and $FeCl_3$; $SnCl_4$ has proved particularly advantageous.

Solvents usable in the present coupling reaction are generally halogenated hydrocarbons, ethers or aromatic hydrocarbons. Halogenated hydrocarbons such as dichloromethane, chloroform, trichloroethane and higher homologues are preferred. Dichloromethane is particularly preferred.

In the present invention, the triazole (I), the protected ribofuranose (II) and the Lewis acid (IV) are generally used in a molar ratio of 1-2 moles of I and 1-1.5 moles of IV, for every mole of II. The molar reaction ratios preferably used in the present process provide for 1-1.2 moles of I and 1-1.1 moles of IV for every mole of II.

The coupling reaction according to the present invention is generally conducted at a temperature of between −10° C. and the reflux temperature of the solvent. Preferably, the reaction mixture is cooled to a temperature of between +5 and +20° C. during the addition of the Lewis acid and is afterwards heated to reflux.

The product of the coupling reaction of formula III is customarily isolated according to conventional procedures, known to an expert in the field, such as, for example, extraction with suitable solvents, concentration of the organic phase by evaporation and filtration of the raw product thus precipitated. The raw product is preferably used as such in the subsequent stages or, alternatively, it can be purified, for example through crystallisation or chromatography.

The process for the preparation of ribavirin according to the present invention finally provides for the removal of the Pg protecting groups and, optionally, the conversion of the $R_2$ group, of the intermediate product of the formula III, into a carboxyamide group.

The removal of the Pg protecting groups is performed under standard conditions, which vary depending on the chemical nature of the group itself. In general, see removal conditions described by T. Green and P. Wuts in the text cited above, "Protecting Groups in Organic Synthesis", chapter 2, page 17, 3rd Ed. (1999).

For example in the case where the protecting group is an ester, its removal will be effected by alcoholysis in basic catalysis conditions. In particular, when Pg represents an acetyl group, de-protection is preferably performed with methanol in the presence of sodium methylate.

Finally, if $R_2$ is different from $CONH_2$, the synthesis of ribavirin will be completed through conversion of the $R_2$ group of the intermediate product of formula III already de-protected on the sugar, into a carboxyamide group.

Said conversion will be conducted under different conditions based on the meaning of $R_2$ and in any case through reactions well known to an expert in the field and not binding for the purposes of the present invention. By way of example there may be cited the reactions of preparation of amides reported by J. March in "Advanced Organic Chemistry", page 1152, 3rd Ed. (1985).

In particular, when $R_2$ represents carbomethoxy, it is preferred to perform the aforesaid transformation of the de-protected intermediate product III by treatment with ammonia in methanol. This reaction of ammonolysis may be conducted at a pressure of between 1 and 4 atmospheres, preferably at 1.9-2.5 atm.

Alternatively, it is possible to proceed at the same time with the de-protection of the sugar and with the conversion of the $R_2$ group of the compound of formula III into a carboxyamide group, to give ribavirin directly.

For example, ribavirin may be prepared directly by treatment of the intermediate product III, in which Pg represents acetyl and $R_2$ represents carbomethoxy, with ammonia in methanol, as described in *J. Med. Chem.* 1972. Vol. 15, No. 11, 1150-1154.

According to a preferred embodiment, to the pre-cooled suspension of the triazole of formula I and of the protected ribose of formula II in the preselected solvent, the Lewis acid IV is added while stirring and in an inert atmosphere, maintaining the temperature below 20° C.

When the addition is finished, the reaction is brought to reflux until completed. The reaction is terminated by the addition of acidified water, checking that the temperature does not exceed 20° C. The phases are separated, the organic phase is washed again with acidified water and the aqueous phases are extracted several times with organic solvent. The organic phases are concentrated under vacuum and the raw product IV is isolated through precipitation by the addition of a co-solvent, partial evaporation and filtration of the solid.

The solid thus obtained is taken up with the preselected alcohol and de-protected, according to conventional techniques, preferably by alcoholysis in the presence of the corresponding sodium alcoholate, and then converted into ribavirin, by ammonolysis in an alcoholic medium. The ribavirin is then isolated by crystallisation, preferably from aqueous methanol; according to the best embodiment of the invention, said crystallisation is carried out at a temperature below 50° C. and using from 2 to 5 volumes of methanol per volume of water.

As will be seen from the following examples, which should not be regarded as limiting the invention, the present process makes it possible to prepare ribavirin with high yields and purities without having recourse to any preliminary stage of activation of the triazole ring, with obvious advantages in terms of time, purity and raw materials.

The process of the present invention further makes it possible to prepare ribavirin as a single polymorphous form, as required by the health authorities. Ribavirin in fact exists in two distinct polymorphous forms; the first, obtained by crystallisation from aqueous ethanol, has a melting point of 166-168° C.; the second, obtained by crystallisation from ethanol, has a melting point of 174-176° C. (Merck Index 11th edition). With the process according to the present invention, ribavirin is obtained exclusively in the first form (or that having a melting point of 166-168° C.), without any trace of the second.

EXAMPLES

Synthesis of the methyl ester of 1-(2,3,5-tri-O-acetyl-β-D-ribofuranosyl)-1H-1,2,4-triazole-3-carboxylic acid (triacetylribavirin, 3-carbomethoxy, TARC, IV, PG=$CH_3CO$, $R_2$=$COOCH_3$)

In a 6000 ml, 4-neck anhydrous reactor equipped with thermometer, condenser and mechanical stirrer, there are placed, while stirring and with a flow of nitrogen, 1680 ml of dichloromethane, 400 g of tetra-acetylribose (Fluka) and 185.2 g of 3-carbo-methoxytriazole. The mixture is cooled to about 5° C. and 360 g of tin tetrachloride are added to the suspension in a thin stream while stirring. The exothermy of the reaction is controlled by cooling with an ice bath so that the temperature does not exceed 15-20° C. and, when the addition is finished, the reaction mixture is heated to reflux for 2 hours. It is cooled to 20° C. with a water and ice bath in 15 minutes. Then 30% hydrochloric acid (176.7 ml) and water (1503.3 ml) are added at a temperature below +20° C. and stirring is carried out for 45 minutes; the mixture is left to dephase for 15 minutes, then the upper aqueous phase is separated from the rich organic phase which is subsequently treated with 30% hydrochloric acid (176.7 ml) and water (1503.3 ml). After 45 minutes' stirring, the mixture is left to dephase for 15 minutes and the upper aqueous phase is separated from the rich organic phase, which is subsequently treated with 30% hydrochloric acid (176.7 ml) and water (1503.3 ml). After 45 minutes' stirring, the mixture is left to dephase for 15 minutes and the phases are separated: the organic phase is distilled at atmospheric pressure (internal T approx. 45° C.), and to the oily residue 3000 ml of toluene are added and the mixture is distilled under vacuum at about 200 mbar of residual pressure to a stirrable moist paste. It is cooled to 5-10° C. for 2 hours and filtered over a Buchner filter while washing with toluene. 524 g of moist product are obtained, equal to 392 g dry product.

Synthesis of the methyl ester of 1-β-D-ribofuranosyl-1H-1,2,4-triazole-3-carboxylic acid (methyl ester of ribavirin, RIBEST, IV, Pg=H, $R_2$=$COOCH_3$)

To the moist solid residue thus obtained, 2000 ml of methanol are added and it is checked that the moisture content is below 0.2%. The mixture is cooled to 10° C. and 34 g of sodium methoxide in 30% methanol are added in 30 minutes. A clear yellow solution is obtained which is maintained while stirring in an inert atmosphere for 3 hours at 10° C. Then 11.4 g of glacial acetic acid are added and the mixture is distilled under vacuum (from 300 mbar to 50 mbar) at 30-35° C. to an oily residue. The residue is taken up again with methanol, distilling under vacuum to an oily residue.

Synthesis of Ribavirin (l)

To the residue thus obtained, 1000 ml of methanol and 64 g of gaseous ammonia are added and the mixture left for 4 hours at 20° C. while stirring; there is precipitation of product in the course of the reaction. Distillation under reduced pressure (200 mmHg; internal T 40° C.) is carried out to about half volume and 200 ml of water are added; heating to 60°-70° C. is carried out until dissolved and 400 ml of methanol are added. The mixture is cooled to 0°-5° C. for 4 hours and the solid is filtered over a Buchner filter while washing with methanol; 300 g of moist raw Ribavirin are obtained and this is crystallised without desiccation.

Crystallisation 200 ml of water are placed in a 1000 ml reactor equipped with stirrer and condenser and are heated to 40°-50° C. while adding, a little at a time, 300 g of moist ribavirin (equal to 206 g dry product), heating to a maximum temperature of 60° C. while stirring until dissolved. Then 500 ml of methanol are added; the resultant pH is equal to 7-8. Cooling to around 40°-45° C. is carried out, bringing about the precipitation of the product and this is left to crystallise for one hour while stirring at ambient temperature: formation of abundant precipitate. Cooling to 5° C. is carried out for 2 hours and the product is filtered over a Buchner filter, while washing with 200 ml of methanol. 300 g of moist crystallised Ribavirin are obtained which are dried at 60° C. under vacuum overnight to give 197.5 g of dry product.

| Analytical data: | |
|---|---|
| Appearance: | crystalline white monomorphous powder, |
| $[\alpha]_D$(10 mg/ml; $H_2O$): | −35.6° |
| Melting point: | 166-168° C. |
| HPLC purity: | 99.8% |
| NMR (Brucker 300 MHz, $d_6$-DMSO): | the $^1H$ and $^{13}C$ NMR spectra confirm the structure of the ribavirin. |

The NOESY spectrum excludes the presence of α anomer and demonstrates that the regioisomer obtained is that in which position 1 of the ribose is bonded to the nitrogen atom in 1 of the triazole ring. DSC analysis finally confirms the total absence of other polymorphous forms (even traces).

The invention claimed is:

1. A process for the preparation of a compound of formula (IV)

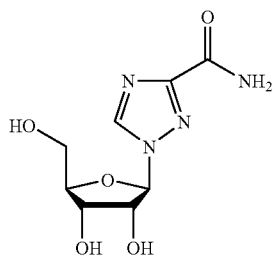

which consists of:
a) the reaction of a triazole of the formula

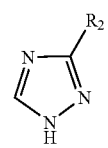

wherein $R_2$ represents a $C_1$-$C_4$ alkoxycarbonyl, arylalkoxycarbonyl, carboxyl, cyano, carboxyamide group with a protected ribofuranose of the formula

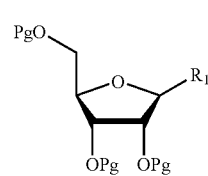

wherein Pg represents a group protecting the hydroxyl function and $R_1$ represents a leaving group selected from among $C_1$-$C_4$ acyloxy, aryloxy and halogen;

in the presence of from 1 to 1.5 moles of a Lewis acid for every mole of (II) and a solvent selected from the group consisting of a halogenated hydrocarbon, an ether, an aromatic hydrocarbon, and mixtures thereof, said solvent having a reflux temperature, said reaction step a) performed at a reaction temperature between −10° C. and the reflux temperature of the solvent; and b) the removal of the Pg groups and the conversion of the $R_2$ group of the compound obtained of the formula

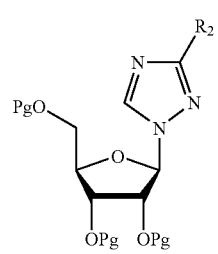

wherein Pg and $R_2$ have the meanings given above, into a carboxyamide group, to give the compound of formula (IV), wherein the triazole (I), ribofuranose (II), and solvent are provided to the reaction step a) as a pre-cooled suspension and the Lewis acid is added to the pre-cooled suspension while maintaining a temperature below 20° C.

2. A process according to claim 1, wherein $R_2$ represents a $C_1$-$C_4$ alkoxycarbonyl group.

3. A process according to claim 1, wherein Pg represents acetyl, benzoyl or benzyl.

4. A process according to claim 1, wherein $R_1$ represents a group selected from group consisting of chlorine, bromine $C_1$-$C_4$ acyloxy, and mixtures thereof.

5. A process according to claim 1, wherein Pg represents acetyl, $R_2$ represents a carbomethoxy group and $R_1$ represents an acetoxy group.

6. A process according to claim 1, wherein the Lewis acid is selected from the group consisting of $AlCl_3$, $SbCl_5$, $BF_3$, $SnCl_4$, $FeCl_3$, and mixtures thereof.

7. A process according to claim 1, wherein the reagents in stage a) are used in a molar ratio of 1-2 moles of I and 1-1.5 moles of Lewis acid to every mole of II.

8. A process according to claim 1, wherein the compound of formula (IV) is isolated by crystallisation from aqueous methanol.

9. A process according to claim 7, wherein said crystallisation is cried out at a temperature below 50° C. and using from 2 to 5 volumes of methanol per volume of water.

10. A process according to claim 2, wherein $R_2$ represents a carbomethoxy group.

11. A process according to claim 3, wherein Pg represents acetyl.

12. A process according to claim 4, wherein $R_1$ represents an acetoxy group.

13. A process according to claim 6, wherein the Lewis acid is $SnCl_4$.

14. A process according to claim 7, wherein the reagents in stage a) are used in a molar ratio of 1-1.2 moles of I and 1-1.1 moles of Lewis acid to every mole of II.

15. A process for the preparation of a compound of the formula (IV)

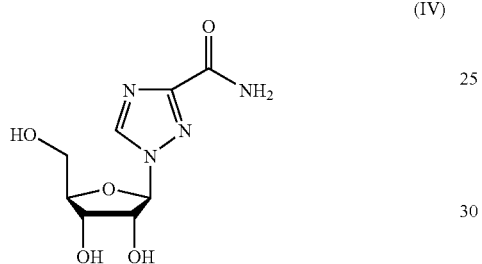

which consists of:
a) the reaction of a triazole of the formula

wherein $R_2$ represents a $C_1$-$C_4$ alkoxycarbonyl, arylalkoxycarbonyl, carboxyl, cyano, carboxyamide group with a protected ribofuranose of the formula

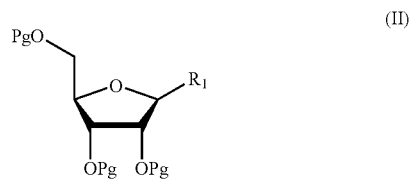

wherein Pg represents a group protecting the hydroxyl function and $R_1$ represents a leaving group selected from among $C_1$-$C_4$ acyloxy, aryloxy and halogen;

in the presence of a Lewis acid selected from the group consisting of $AlCl_3$, $SbCl_5$, $BF_3$, $SnCl_4$ $FeCl_3$, and mixtures thereof and a solvent consisting of a halogenated hydrocarbon, said solvent having a reflux temperature, said reaction step a) performed at a reaction temperature between −10° C. and the reflux temperature of the solvent; and b) the removal of the Pg groups and the conversion of the $R_2$ group of the compound obtained of the formula

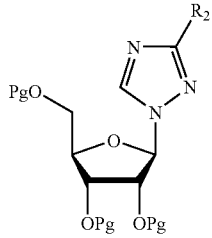

wherein Pg and $R_2$ have the meanings given above, into a carboxyamide group, to give the compound of formula (IV).

16. A process according to claim 15, wherein said halogenated hydrocarbon is selected from the group consisting of dichloromethane, chloroform, trichloroethane, and mixtures thereof.

17. A process according to claim 16, wherein said halogenated hydrocarbon is dichloromethane.

* * * * *